(12) United States Patent
Marshall et al.

(10) Patent No.: US 10,420,659 B2
(45) Date of Patent: Sep. 24, 2019

(54) CORRUGATED MICROPOROUS TISSUE INTERFACE FOR IMPROVED PERFORMANCE AND INFECTION RESISTANCE OF VASCULAR GRAFTS AND OTHER IMPLANTABLE DEVICES

(71) Applicant: Healionics Corporation, Seattle, WA (US)

(72) Inventors: Andrew J. Marshall, Seattle, WA (US); Brandt Scanlan, Seattle, WA (US); Max Maginness, Seattle, WA (US); Adrienne Oda, Seattle, WA (US); Michael J. Connolly, Seattle, WA (US); Chad MacDonald, Seattle, WA (US)

(73) Assignee: HEALIONICS CORPORATION, Seattle, WA (US)

( * ) Notice: Subject to any disclaimer, the term of this patent is extended or adjusted under 35 U.S.C. 154(b) by 0 days.

(21) Appl. No.: 15/687,404

(22) Filed: Aug. 25, 2017

(65) Prior Publication Data

US 2018/0055668 A1  Mar. 1, 2018

Related U.S. Application Data

(60) Provisional application No. 62/380,087, filed on Aug. 26, 2016, provisional application No. 62/380,111, (Continued)

(51) Int. Cl.
*A61F 2/91* (2013.01)
*A61F 2/00* (2006.01)
(Continued)

(52) U.S. Cl.
CPC .............. *A61F 2/91* (2013.01); *A61F 2/0077* (2013.01); *A61F 2/06* (2013.01); *A61F 2/064* (2013.01);
(Continued)

(58) Field of Classification Search
CPC .. A61F 2/91; A61F 2/0077; A61F 2/06; A61F 2/064; A61F 2/848;
(Continued)

(56) References Cited

U.S. PATENT DOCUMENTS

| 4,604,762 A | 8/1986 | Robinson |
| 5,282,847 A | 2/1994 | Trescony et al. |

(Continued)

FOREIGN PATENT DOCUMENTS

| WO | 2013/021215 A1 | 2/2013 |
| WO | 2015/127254 A1 | 8/2015 |

OTHER PUBLICATIONS

International Search Report and Written Opinion of the International Searching Authority, dated Nov. 8, 2017, for International Application No. PCT/US2017/048763, 15 pages.

*Primary Examiner* — Christopher D. Prone
*Assistant Examiner* — Tiffany P Shipmon
(74) *Attorney, Agent, or Firm* — Seed IP Law Group LLP

(57) ABSTRACT

Provided herein are implantable devices, such as vascular grafts and access port for hemodialysis, that include a microporous sheath layer having a corrugated outer surface, and use therefore for reducing the risk of infection or stenosis.

7 Claims, 14 Drawing Sheets

Related U.S. Application Data filed on Aug. 26, 2016, provisional application No. 62/421,861, filed on Nov. 14, 2016.

(51) Int. Cl.
*A61F 2/06* (2013.01)
*A61M 1/36* (2006.01)
*A61F 2/848* (2013.01)

(52) U.S. Cl.
CPC ........ *A61M 1/3653* (2013.01); *A61M 1/3655* (2013.01); *A61F 2/848* (2013.01); *A61F 2210/0076* (2013.01); *A61F 2220/0008* (2013.01); *A61F 2230/0069* (2013.01); *A61F 2250/0024* (2013.01)

(58) Field of Classification Search
CPC ...... A61F 2210/0076; A61F 2230/0069; A61F 2250/0024; A61M 1/3656; A61M 1/3655
See application file for complete search history.

(56) References Cited

U.S. PATENT DOCUMENTS

| | | | |
|---|---|---|---|
| 8,318,193 B2 | 11/2012 | Ratner et al. | |
| 8,647,393 B2 | 2/2014 | Marshall et al. | |
| 2004/0182511 A1* | 9/2004 | Rakos ..................... | A61F 2/06 |
| | | | 156/287 |
| 2011/0257623 A1* | 10/2011 | Marshall ................ | A61L 27/56 |
| | | | 604/500 |

* cited by examiner

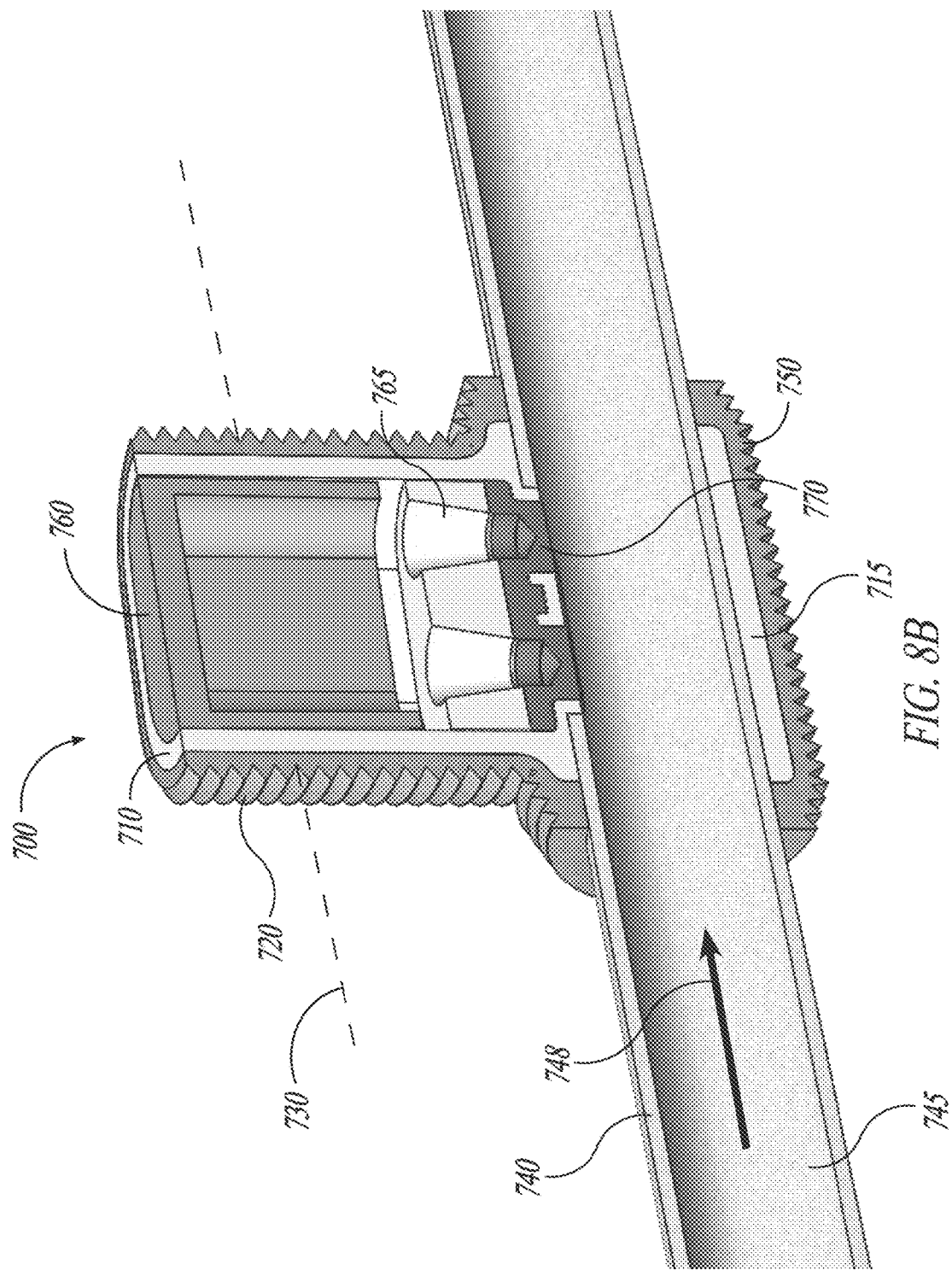

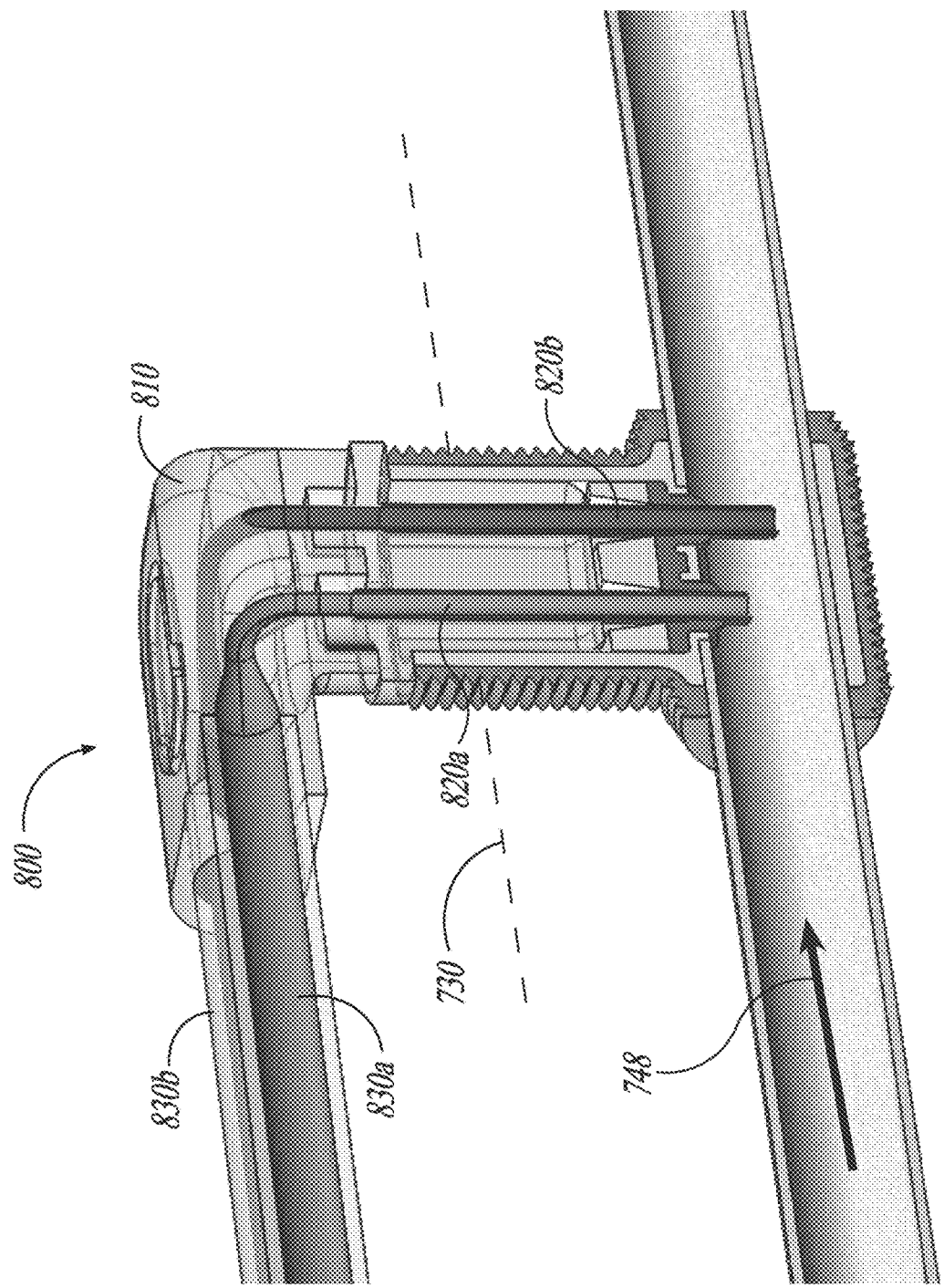

CORRUGATED MICROPOROUS TISSUE INTERFACE FOR IMPROVED PERFORMANCE AND INFECTION RESISTANCE OF VASCULAR GRAFTS AND OTHER IMPLANTABLE DEVICES

CROSS-REFERENCES TO RELATED APPLICATIONS

This application claims the benefit under 35 U.S.C. § 119(e) of U.S. Provisional Patent Application Nos. 62/380,087 and 62/380,111, filed Aug. 26, 2016; and 62/421,861, filed Nov. 14, 2016, which applications are incorporated herein by reference in their entireties.

STATEMENT OF GOVERNMENT INTEREST

This invention was made with government support under Grants No. R44DK103512 and No. R44HL126256, awarded by the National Institutes of Health; and Contract No. W81WH-15-C-0011, awarded by the Department of Defense under the Defense Health Program. The government has certain rights in the invention.

BACKGROUND

Technical Field

This invention generally relates to synthetic vascular grafts, such as artificial blood vessels. It also relates to skin-breaching implantable devices.

Synthetic vascular grafts are artificial tubular blood conduits or patches. They are routinely used as arteriovenous shunts to present a suitable vascular access site for hemodialysis treatment. They are also commonly used to replace or repair diseased segments of natural arteries or veins.

To form an anastomosis with a native blood vessel, a vascular graft is directly connected (e.g., by suturing) at the ends of the graft to the cut edges of a native vessel ("end-to-end") or to an incision in the side of the native vessel ("end-to-side").

The most common vascular graft materials include porous expanded polytetrafluoroethylene (ePTFE) and porous polyethylene terephthalate (Dacron®). They can also be made from porous elastomeric materials such as silicone or polyurethane.

The most common complication with vascular grafts is stenosis, i.e., a narrowing or stricture at the outflow anastomosis, which leads to thrombosis and occlusion of the graft. The occlusive failure of the grafts can be especially severe for replacements of small caliber vessels (less than 6 mm internal diameter), limiting the use of prosthetic grafts in these cases.

The second most common complication with vascular grafts (and the most serious problem when it occurs) is infection. Infections of vascular grafts can progress to bloodstream infections, which can be life-threatening.

Infection is especially common in arteriovenous shunts for hemodialysis access. These types of vascular grafts must be repeatedly cannulated with large-diameter needles at least three times weekly in order to provide vascular access with high blood flow for hemodialysis treatment. With each needle stick, bacteria are dragged from the skin into the wall of the graft. Even if the outside of the skin is thoroughly disinfected prior to cannulation, bacteria residing in the hair follicles of the skin are inevitably transferred to the wall of the vascular graft, potentially seeding infection.

A vascular graft's vulnerability to infection may be further worsened by the fibrotic Foreign Body Response (FBR) that occurs around the device in the initial weeks of healing following implantation. The FBR results in the outer surface of the graft being encapsulated with a dense, avascular layer of collagenous fibrotic tissue. When the outer surface of the device becomes colonized by bacterial biofilm, the fibrotic capsule isolates the device from the surrounding tissues and impedes access for the natural immune defense cells to reach the bacterial biofilm at the device surface.

The FBR also contributes significantly to the stenosis problem. The fibrotic capsule contracts around the device to generate a mechanical constriction effect that stiffens the graft wall. This exacerbates the mechanical mismatch between the vibrating pulsatile blood and the now constricted wall, and increases oscillating shear stresses at the luminal surface. The oscillating wall shear stresses cause the layer of neointimal hyperplasia tissue that forms on the inner graft wall to progressively thicken, leading to stenosis.

U.S. Published Application No. 2015/0238306, in the name of Healionics Corporation (the assignee of the present application), herein incorporated by reference, describes a three-layer vascular graft constructions that are advantageous over conventional vascular grafts; these designs address the outflow stenosis problem by employing an outer surface layer capable of greatly reducing fibrotic encapsulation and constriction effects. The outer surface layer is attached to an inner layer (e.g., an ePTFE graft) by an intermediate adhesive layer. However, the intermediate adhesive layer is typically nonporous elastomeric silicone, which may reduce the kink resistance of the overall graft. The nonporous silicone layer also restricts access for immune defense cells to reach the ePTFE surfaces of the inner layer.

There remains an unmet need for a vascular graft with high reliability and high resistance to infection.

BRIEF SUMMARY OF THE INVENTION

Disclosed herein are synthetic vascular grafts capable of addressing the above limitations by maintaining long-term patency and long-term enhanced resistance to infection. Implantable skin-breaching devices with enhanced infection resistance are also disclosed.

The implantable devices disclosed herein comprise a microporous tissue-contacting layer with corrugated outer surface contour. The corrugated outer surface contour, when combined with other key features such as optimized geometry of the microporosity and soft elastomeric material composition, confers certain performance advantages over prior art devices, particularly for devices that interface with skin (e.g., insertion through or exit from skin). Currently known devices that employ certain tissue-integrating features at the exit site interface, such as Dacron velour, woven textiles, or knit fabrics, inevitably develop bacterial biofilm and harbor infection during long-term use. In contrast, the implantable devices described herein address the above technical challenges.

One embodiment provides a tubular implantable device comprising a two-layer composite wall defining a longitudinal passageway, wherein the two-layer composite wall includes an inner fluid-contacting layer and a microporous sheath layer having a corrugated outer surface, and wherein the microporous sheath layer is formed of a biocompatible elastomeric biomaterial having an open-pore network of interconnected pores extending from an interface between the inner fluid-contacting layer and the microporous sheath layer to the corrugated outer surface. As discussed in further detail herein, the corrugated outer surface of the microporous sheath layer facilitates tissue integration and promotes long-term infection resistance.

The tubular implantable device typically has a longitudinal passageway that allows fluid (e.g., blood) to flow through, as in a vascular graft. Circumferentially, it may have a regular or irregular shaped cross-section. The cross-sections may be circular (as in most of the vascular grafts), ellipsoid, square, trapezoid or irregular geometric shapes. The longitudinal passageway may also serve as a hemodialysis access port for housing the cannulas (arterial and venous).

In one particularly advantageous embodiment, the tubular implantable device is a vascular graft that comprises a two-layer composite wall including: an inner blood-contacting layer, which may be composed of ePTFE, porous Dacron, or other microporous material well-suited for vascular grafts; and a microporous sheath layer having a corrugated outer surface, the microporous sheath layer being formed of an open-pore microporous biomaterial, wherein the inner fluid-contacting layer provides structural strength and has pore sizes well-suited for minimizing thrombotic deposition and limiting initial serum leakage following implantation; wherein the corrugated microporous sheath is formed from a biocompatible elastomeric biomaterial and comprises an open-pore network of interconnected pores extending from the corrugated outer surface of the vascular graft inward to the boundary/interface between the two layers; wherein substantially all the interconnected pores of the microporous sheath are each connected to at least 2 other pores, the mean diameter of the pores being between about 5 micrometers and about 90 micrometers, and any two adjacent pores are connected by a throat, a mean throat diameter being at least 5 micrometers; and wherein the outer surface contour of the microporous sheath is corrugated or ribbed, such that the thickness of the sheath layer (as a function of distance measured longitudinally along the direction of blood flow) alternates between a major layer thickness and minor layer thickness.

In particular, the pore geometry of the corrugated microporous sheath is optimized to attract a high concentration of macrophage cells into its pores when surgically implanted into soft tissue. An especially suitable material is STAR® (Sphere Templated Angiogenic Regeneration) Biomaterial, as described in U.S. Pat. No. 8,318,193, which is incorporated herein by reference in its entirety. Briefly, the suitable biomaterial is formed of an elastomeric material having a plurality of substantially interconnected pores as shown FIG. 1.

The vascular graft comprises a corrugated microporous sheath as the outer layer, which construction confers several advantages over prior art designs.

The corrugated outer surface contour for the elastomeric microporous sheath enables the graft to be routed in a loop configuration or in a tight bending radius without the elastomeric layer compromising the graft's kink resistance and without compromising the pulsatility of the graft. As used herein in, pulsatility is defined as the reversible increase in luminal cross-sectional area for a given increase in blood pressure.

In addition, the corrugated microporous sheath, which forms the outer layer of a vascular graft, improves infection resistance via multiple mechanisms of action.

Moreover, the sheath layer employs a continuously porous layer construction having pore sizes optimized for concentrating macrophages. This feature ensures that substantially all of the internal pore surfaces in the sheath layer is coated with antimicrobial macrophages. The corrugated exterior contour allows this continuously porous layer to be made from elastomeric materials without compromising the graft's kink resistance, so that the macrophages have numerous continuous pathways through the material that connects the outer tissue-contacting surface to the outer surface of the inner structural layer of the graft. Thus, tissue ingrowth through the wall of the graft is not inhibited.

These continuous pathways through the microporous sheath layer do not become blocked by fibrotic collagenous tissue due to the optimized pore geometry. Rather, the continuous pathways promote the development of a robust capillary network through the sheath layer. This capillary network facilitates transport of macrophages, neutrophils, and other immune defense cells through the material, which can help eliminate bacteria and prevent the formation of bacterial biofilms along the graft surfaces.

The capillary network that forms in the corrugated microporous sheath layer helps to disrupt the FBR and suppress fibrotic encapsulation. This network further facilitates the transport of immune defense cells through the wall of the graft, and improves access for immune cells to reach the outer surface of the graft from the surrounding tissue.

The corrugated microporous sheath layer also helps to resist infection when hemodialysis needles are used to cannulate the graft, by limiting the amount of blood that leaks out through the wall of the graft into the surrounding tissue. In a conventional vascular graft, the blood that leaks out through the wall clots to form a hematoma, which eventually seeds bacterial biofilm, leading to increased infection risk. The corrugated microporous sheath is capable of acting like a sponge, wicking the leaked blood into its interconnected micropores. The wicking or sponge effect can prevent the blood from escaping into the surrounding tissue.

The sponge effect of the corrugated microporous sheath can provide the added advantage of reducing the time required to reach hemostasis following cannulation, providing a self-sealing effect. The improved sealing may allow the graft to be cannulated earlier after placement, thereby reducing the length of reliance on a central venous catheter for temporary vascular access, which carries a high-infection risk.

While certain prior art grafts employ a self-sealing nonporous elastomer or gel layer, such as the Gore ACUSEAL® Vascular Graft (WL Gore & Associates Inc, Medical Products Division, Flagstaff Ariz.), such self-sealing nonporous layers tend to trap bacterial biofilms, thereby sheltering the bacteria from immune defense cells and potentially leading to infection. Thus, compared to the prior art self-sealing grafts, the vascular grafts described herein achieve improved self-sealing and hemostasis through the sponge effect.

The corrugated microporous sheath further helps to improve infection resistance by limiting the adverse effects of suture hole leakage (i.e., key-holing) at the anastomosis. Suture hole leakage is reduced without the need for a bacteria-sheltering nonporous self-sealing layer.

Suppression of the FBR by the corrugated microporous sheath also helps to reduce the progression of neointimal hyperplasia inside the graft lumen near the outflow anastomosis. Due to the corrugated outer surface contour, the FBR is suppressed without compromising kink resistance.

In various embodiments, the corrugated microporous sheath may be undersized and stretched over the exterior surface of a graft (adhered by compression fit), whereby the graft wall forms the inner fluid or blood-contacting layer. In other embodiments, the corrugated microporous sheath may be selectively adhered with glue or other suitable means of adhesion to the exterior of the graft.

In another particularly advantageous embodiment, a vascular graft comprises a single elastomeric corrugated microporous layer defining a fluid passageway, wherein the layer has similar pore structure and features to the corrugated microporous sheath layer of the two-layer embodiment described above.

The single layer elastomeric corrugated microporous vascular graft is particularly advantageous for reconstruction or repair of small caliber vessels.

The single layer corrugated microporous vascular graft is further capable of reliably maintaining patency in challenging repair environments, such as vascular repair of contaminated trauma wounds, and coronary artery bypass grafts. It has multiple advantages over prior art vascular graft designs.

A first advantage of the single layer corrugated microporous vascular graft is that the entire graft can be made from a soft, elastomeric porous material without compromising kink resistance, radial compliance, or pulsatility. Radial compliance and pulsatility are important properties for avoiding mechanical mismatch with the native vessels.

A second advantage of the single layer corrugated microporous vascular graft is that it is capable of promoting endothelialization.

A third advantage of the single layer corrugated microporous vascular graft is that it has excellent resistance to infection.

Another particularly advantageous embodiment of the invention is the use of the corrugated microporous sheath around the skin-breaching component of an implantable skin-breaching device, such as a catheter, ventricular assist device, or a percutaneous port for hemodialysis access.

In this embodiment, the corrugated microporous sheath has similar tightly-controlled pore geometry to the corrugated microporous sheath described for the vascular grafts above. When used as an exit tissue interface for skin-breaching devices, the corrugated microporous sheath has certain advantages in preventing exit site infection compared to earlier approaches.

A first advantage of the corrugated microporous exit site interface layer is that it promotes vascularized ingrowth. In particular, the vascularized ingrowth occurs not only in the portion of the biomaterial that is buried under the skinline (i.e., below the interface where the edge of the epidermis meets the outer surface of the biomaterial), but also reaches into the portion above the skinline. In other words, the continuously porous construction allows the ingrown capillaries to connect to each other in the regions below and above the skinline.

Moreover, the corrugated microporous exit site interface layer at an exit site interface reduces excessive localized stress which would otherwise be present at the junction at the skin line between the edge of the epidermis and the microporous biomaterial when the device is manipulated, or when the patient exercises or moves the part of their body containing the implanted device. The corrugated microporous exit site interface provides large circumferentially disposed grooves that provide a site for the edge of the epidermis to "nest" in. The skin-breaching device is preferably implanted through an undersized cut generally circular or oval-shaped opening in the skin. Following implantation, the opening in the skin may constrict around the device. Due to the corrugations, the constriction effect causes the edge of the epidermis to seat more securely in the base of a groove, thereby creating a self-stabilizing effect that speeds biointegration. This enables the exit site to seal more quickly, reducing likelihood of infection.

The nesting effect also shields the edge of the epidermis from unfavorable stress concentrations by distributing stresses acting on the skinline interface over a much wider surface area. Especially, axial stresses acting on the skin-breaching device can be transmitted to the cushioned ridges underlying the skinline, which is integrated with the underside of the epidermis as well as the dermal tissue.

Furthermore, the corrugated microporous exit site interface enables viable vascularized integrated tissue to extend outward into the portion of the biomaterial above the skinline. This advantageously creates additional protection against infection, and reduces the amount of undesirable dead scab tissue that tends to occupy the region outside the exit site interface for conventional skin-breaching devices.

BRIEF DESCRIPTION OF THE DRAWINGS

FIG. 4A shows schematic drawing of an end view; FIG. 4B shows a side view photo.

FIGS. 8A-8C show a schematic drawing for the embodiment of the present invention comprising a skin-beaching hemodialysis access port with corrugated microporous silicone elastomer covering the skin-breaching component of the device. FIG. 8A shows an isometric view; FIG. 8B shows an isometric cross-section view with the device capped between dialysis sessions; FIG. 8C shows an isometric cross-section view with the device cannulated for a dialysis session.

FIG. 11A shows a prior art monolayer of granular microporous "peaks" with nonporous "valley" floors. FIG. 11B shows a prior art continuously microporous "peaks-and-valleys" material. FIG. 11C shows the continuously porous corrugated tissue interface, wherein the groove is continuous and wraps around the entire circumference of the skin-breaching component of the device.

DETAILED DESCRIPTION

To date, there is no synthetic vascular graft that reliably stays open to blood flow, and no synthetic vascular graft that reliably avoids infectious complications. There is also no reliable way to avoid exit site infections of implanted devices having a large-diameter skin-breaching component.

Disclosed herein are implantable vascular grafts capable of preventing the common complications of outflow stenosis and infection. Also disclosed are implantable skin-breaching devices capable of preventing exit site infections.

Each of the embodiments of the present invention comprise the common element of incorporating a tissue-contacting layer of a microporous biomaterial having an outer surface of corrugated or ribbed contour. In various embodiments, the tissue-contacting layer may be a tubular sheath layer over a portion or all of an exterior surface of a tubular device (e.g., a vascular graft), thereby forming a two-layer composite wall construction. In other embodiments, the tissue-contacting layer is a single-layer wall construction defining a fluid (blood) passageway.

Figure 1:
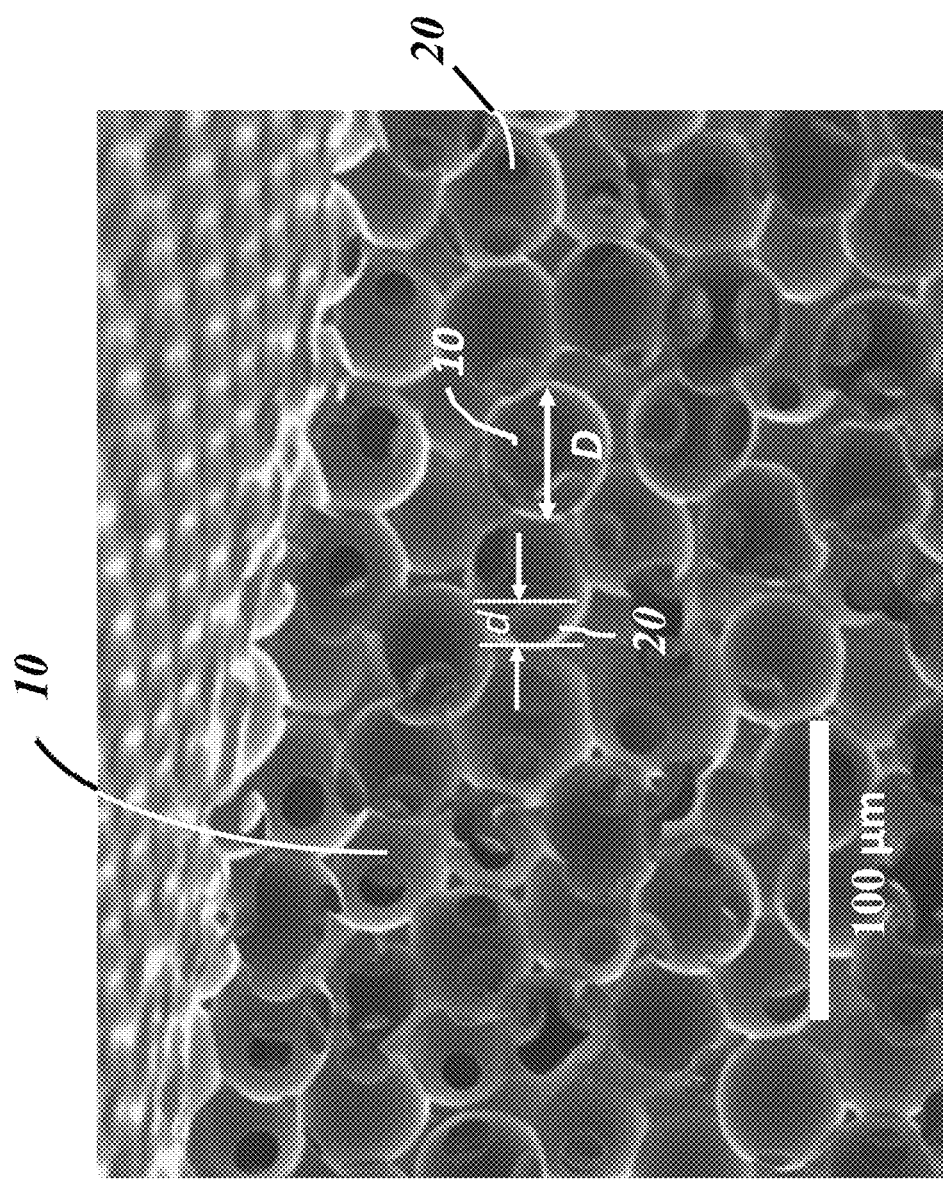
FIG. 1. is a scanning electron microscopy (SEM) image of a known microporous biomaterial with sphere-templated pore geometry.

FIG. 1 is a scanning electron microscopy (SEM) image of a known sphere-templated porous biomaterial (STAR®) that may be used for the layer of the microporous biomaterial described in the present disclosure. The pore structure comprises a network of interconnected void spaces referred to herein as pores 10. Neighboring pores 10 are joined or connected by openings or "throats" 20. The pores 10 can be spherical as in FIG. 1, or they can be any other pore shapes that result in a generally open-cell pore structure. The throats 20 can be circular as in FIG. 1, or they can be any other shapes that consistently define the size of the openings between neighboring pores 10. If the pore throats are not circular, then the throat diameter d is defined as the diameter of the largest spherical object that can pass through the throats 20.

Advantageously, the pore sizes and the throat diameters (i.e., dimensions of the openings between adjoining pores) can be controlled to allow macrophages or neutrophils to infiltrate, as well as enhance the accessible surface areas for the macrophages and neutrophils. Thus, in certain embodiments, substantially all of the interconnected pores (i.e., at least 90%, or at least 95% or at least 98%) in the corrugated microporous biomaterial are each connected to at least 2 other pores, a mean diameter of the pores ("D") being between about 5 and about 90 micrometers, or more preferably between 10 and 40 micrometers, or most preferably between 20 and 40 micrometers. As used herein, "substantially all of the pores" means at least 90%, or at least 95% or at least 98% of all of the pores. In addition, "about" refers to a range of values ±20%, e.g. about 10 micrometers would be 8-12 micrometers.

In accordance with the present disclosure, throat diameter d in the corrugated microporous biomaterial is large enough to permit host macrophages and neutrophils to infiltrate the pore structure. These cells are capable of attacking and destroying bacteria and preventing bacterial colonization. A human macrophage is typically 15-20 microns in diameter, but is capable of squeezing through openings as small as 5 microns in diameter. A neutrophil is similar in size to a macrophage. Accordingly, the throat diameter d should be at least 5 microns. In various embodiments, the throat diameter should be at least 8 microns, or at least 10 microns.

To the extent that throat diameters smaller than 5 microns may be formed in the course of producing the microporous biomaterial (e.g., according to the methods disclosed in U.S. Pat. No. 8,318,193), care should be taken to minimize the percentage of these smaller throat diameters. A bacterial cell is much smaller than a macrophage, typically 1 to 2 microns in size. Pores having throats in the 1 to 5-micron size range can allow bacteria to enter while preventing access to the much larger macrophages and neutrophils that would ordinarily attack and destroy the bacteria. Thus, in certain embodiments, only a very small percentage of throats (less than 2%, more preferably less than 1%) have diameter d in the 1 to 5-micron size range.

In other embodiments, at least 90% of all the throats in the corrugated microporous layer of the device have diameters of at least 5 microns. In various other embodiments, at least 95%, or at least 98% or at least 99% of all the throats in the microporous layer have diameters of at least 5 microns.

A further important feature is that the pore structure has high bioaccessible surface area, where "bioaccessible surface area" is defined as the surface area accessible to macrophages. Surface area is inversely proportional to pore size, so the size of the pores 10 is an important parameter for measuring the bioaccessible surface area. The average or mean pore diameter D should be less than 90 microns, more preferably less than 40 microns, and most preferably less than 35 microns. It is preferable that the pore size be the smallest possible size wherein the pores can be interconnected by throats of the optimal 8 to 15-micron size range. Preferably, the throat diameter d should be about 40% of the pore diameter D, such as between 30% and 45% or between 35% and 45%. When the ratios of the throat sizes to pore sizes are too large (e.g., larger than 45%), the resulting pore structure may become mechanically fragile. Conversely, ratios smaller than 30% may have larger pores and thus lower bioaccessible surface area, so the device does not attract macrophages into its porous interior at effective concentrations for antibacterial defense.

Larger-than-optimal pore diameters are also more likely to become infiltrated with fibrotic tissue after the initial wave of macrophages coats the pore surfaces. Excess fibrotic tissue can limit the accessibility for additional immune defense cells to reach the biomaterial surface when the initial layer of surface-adherent macrophages needs to be refreshed.

The corrugated microporous layer can be made from any polymer. A particularly suitable polymer is silicone rubber. NuSil MED-4830, MED-4840, MED-4850, and MED-4860, (Nusil Technology LLC, Carpinteria, Calif.) are particularly suitable compositions. Other possible biostable materials include polyurethanes, polypropylene, polyethylene, cellulose nitrate, cellulose acetate, polytetrafluoroethylene (PTFE), or hydrogels. In some embodiments, the corrugated microporous layer can be made from a biodegradable polymer.

Most preferably, the corrugated microporous biomaterial should be made from a low durometer elastomer having a durometer value when measured in its nonporous form, ideally about 30 Shore A. A low durometer value combined with porosity is less irritating and less inflammatory to tissues than more rigid materials. And preferably, the elastomeric polymer should have maximum elongation strain greater than 100%, more preferably greater than 300%, and most preferably greater than 500%. In some embodiments, high elongation and high elasticity facilitates needle cannulation through the wall of a vascular graft device with minimal deterioration of the corrugated microporous layer. High elongation and high elasticity is also preferable for ensuring good hemostatic sealing properties in embodiments where needles are pushed through the corrugated microporous layer.

Figure 2:
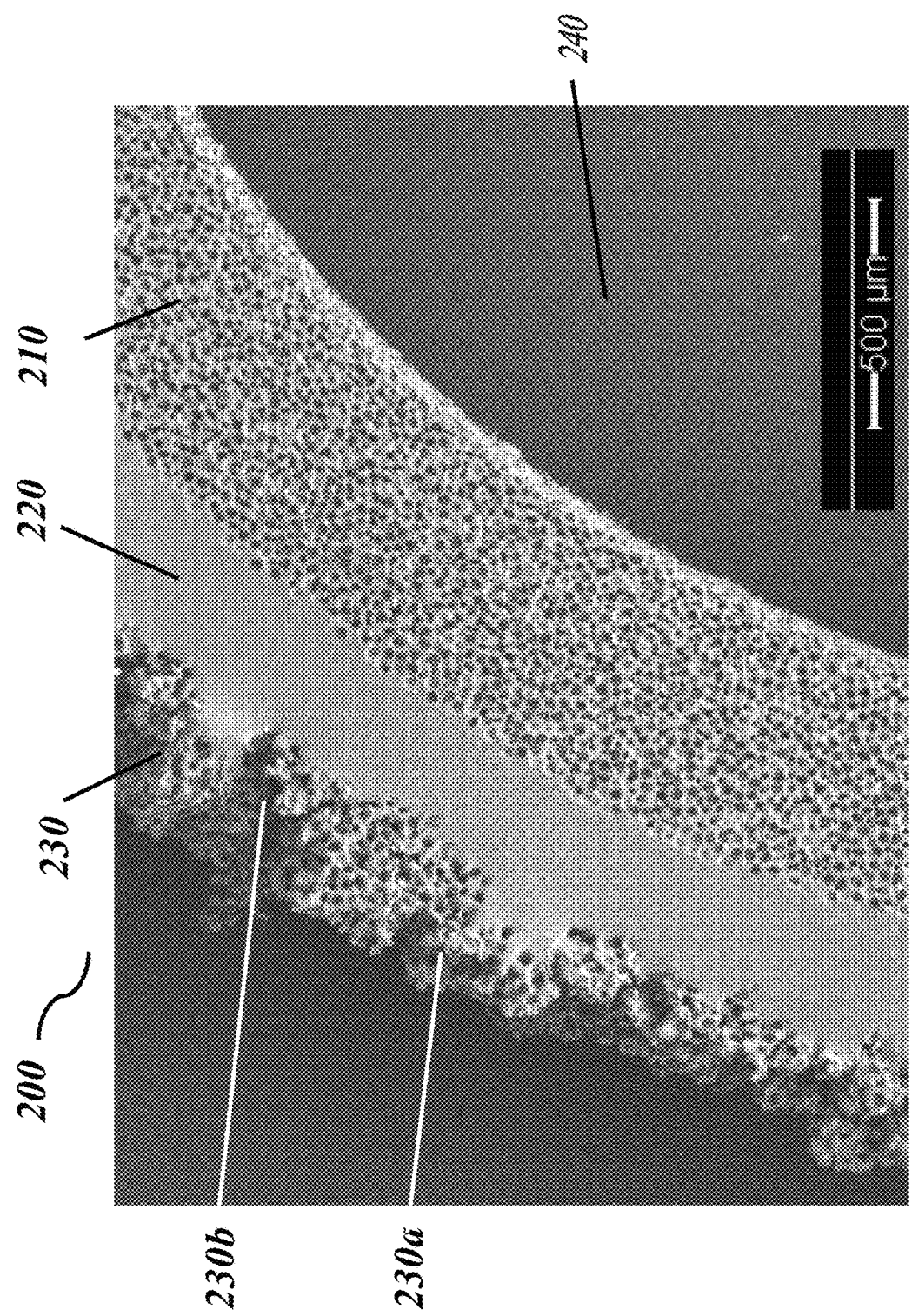
FIG. 2 is a scanning electron microscopy (SEM) image showing the wall cross section of a prior art tri-layer vascular graft composed entirely of elastomeric silicone.

FIG. 2 is a scanning electron microscopy (SEM) image showing the wall cross section of a prior art tri-layer vascular graft 200 composed entirely of elastomeric silicone (see U.S. Published Application No. 2015/0238306). The vascular graft comprises a microporous inner layer 210, comprising the blood contacting surface defining lumen 240, a nonporous middle layer 220, and a textured microporous outer layer 230. The textured outer layer 230 comprises an adhered monolayer of microporous granules 230a separated by valleys 230b. The outer textured microporous layer 230 addresses the problem of outflow stenosis by eliminating constriction forces from the exterior capsule. However, the use of only elastomeric materials renders this vascular graft construction prone to forming kinks along the length of the graft.

Figure 3:
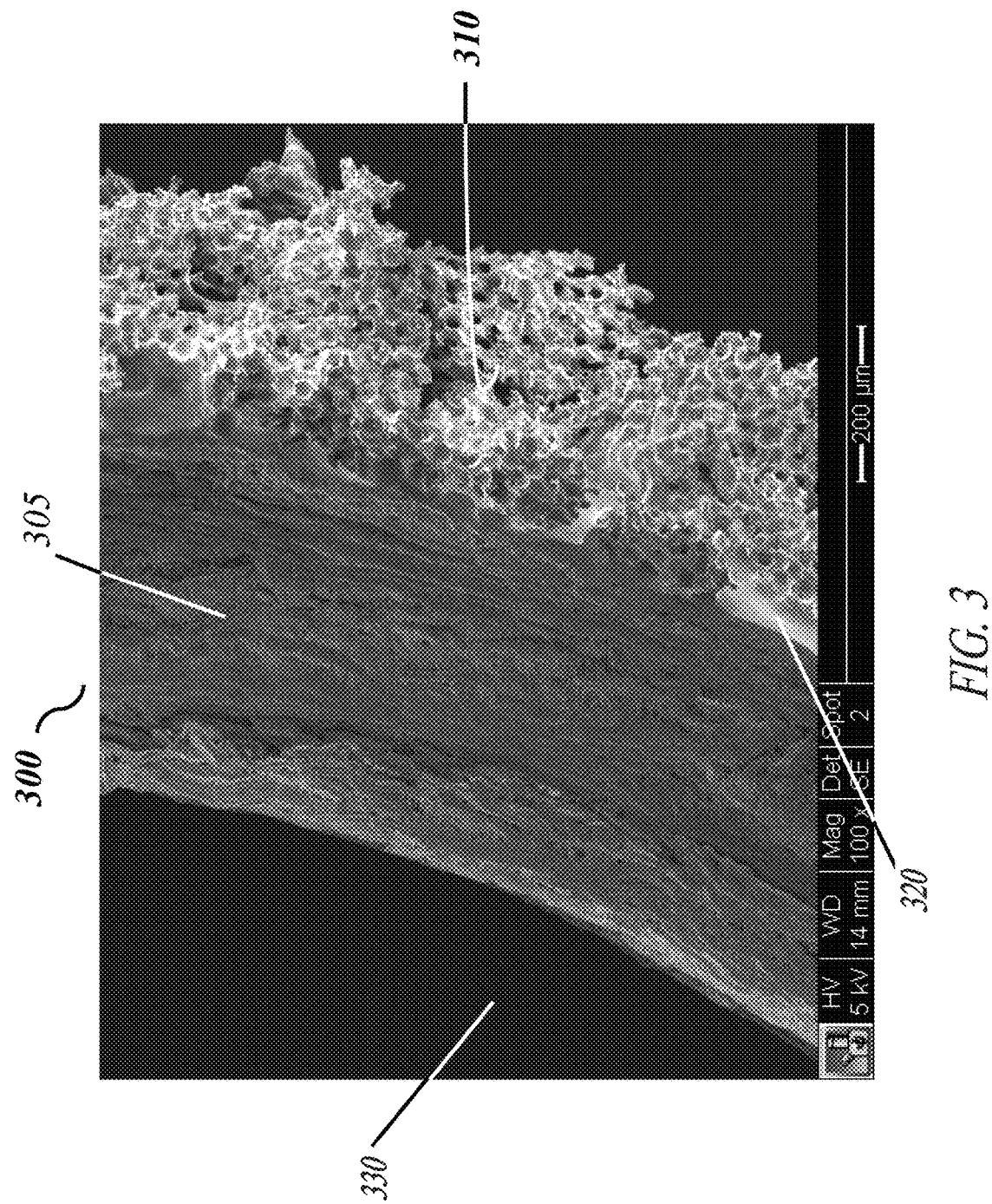
FIG. 3 is a scanning electron microscopy (SEM) image showing the wall cross section a prior art tri-layer vascular graft comprising an expanded polytetrafluoroethylene (ePTFE) inner layer, a nonporous silicone middle layer, and textured granular porous silicone outer layer.

FIG. 3 is a scanning electron microscopy (SEM) image showing the wall cross section of another prior art tri-layer vascular graft 300 comprising an expanded polytetrafluoroethylene (ePTFE) inner layer 305 defining lumen 330, a nonporous silicone middle layer 320, and textured porous silicone outer layer 310. The use of an ePTFE core layer improves the kink resistance compared to an all-elastomer design, but the nonporous elastomeric silicone layer 320 still creates a kink risk, even when this layer is very thin compared to the other layers. The nonporous layer 320 also has the potential of sheltering bacteria in the ePTFE layer 305, because immune cells can only access the inner surface of the nonporous layer 320 from one direction (i.e., from the lumen 330), and because hypoxic and/or cell-nutrient-starved conditions can develop in the ePTFE layer 305 near the surface of the nonporous layer 320.

Figure 4:
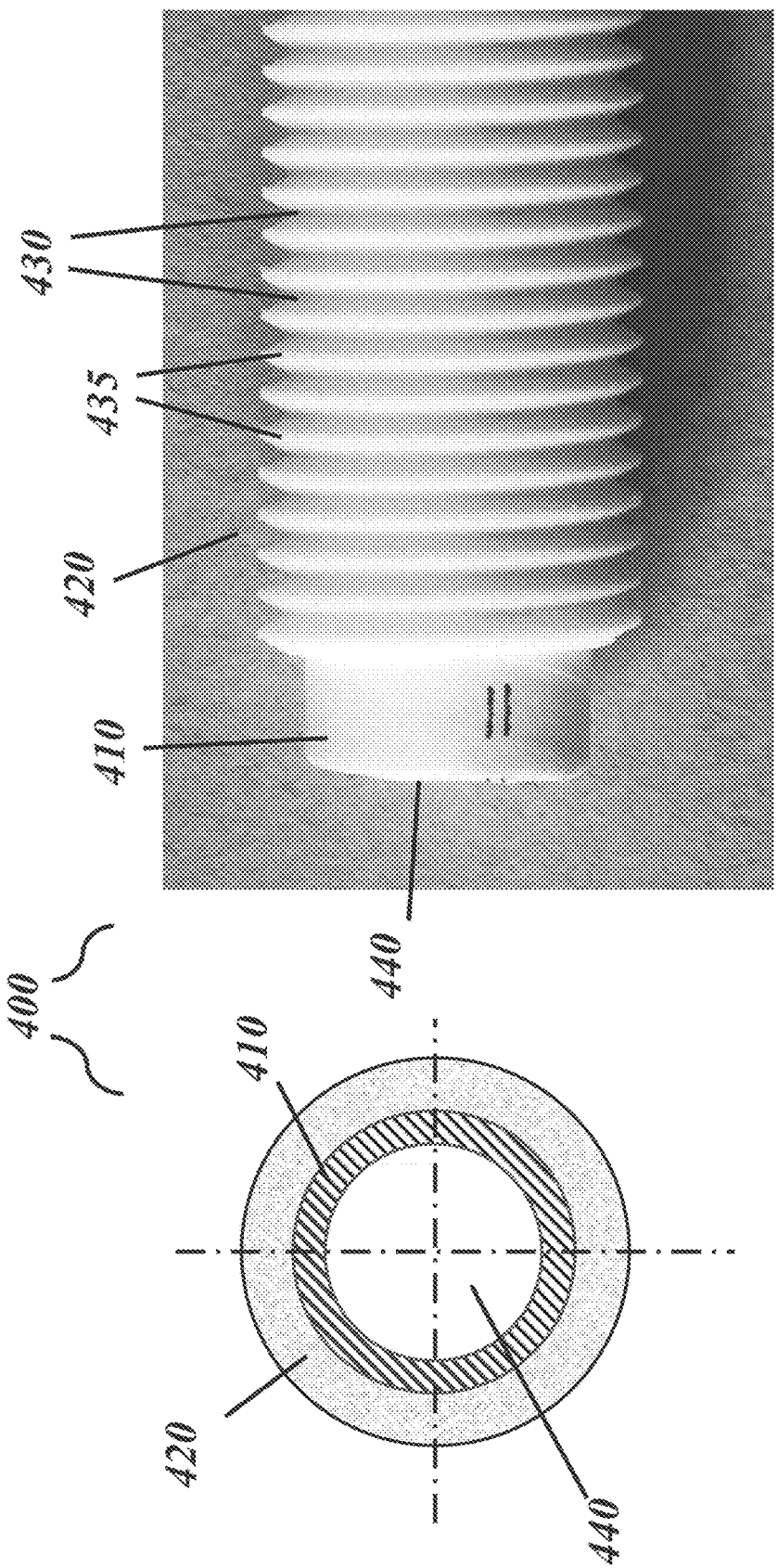
FIGS. 4A-4B show orthogonal views for the embodiment of the present invention comprising a two-layer vascular graft with inner layer of expanded polytetrafluoroethylene (ePTFE) and outer layer of corrugated microporous elastomeric silicone.

FIG. 4 shows orthogonal views according to one embodiment of the present disclosure. As shown, a two-layer vascular graft 400 comprises an inner layer 410 of expanded polytetrafluoroethylene (ePTFE) defining lumen 440, and outer layer 420 of corrugated microporous elastomeric silicone. When viewed from the side, as shown in FIG. 4B, the ridges 435 of the corrugated contour are separated by grooves 430. The layer of this regularly placed ridge-and-groove contour extends all the way around, or at least substantially all the way around the circumference of the device. This embodiment overcomes the usual limitation of kink resistance associated with the incorporation of an elastomeric layer.

It is important that the corrugated contour feature be applied only to a soft microporous sponge layer, and not to any nonporous layers. Limiting the corrugated feature to the soft microporous layer preserves radial pulsatility and wall flexibility of the vascular graft.

Figure 5:
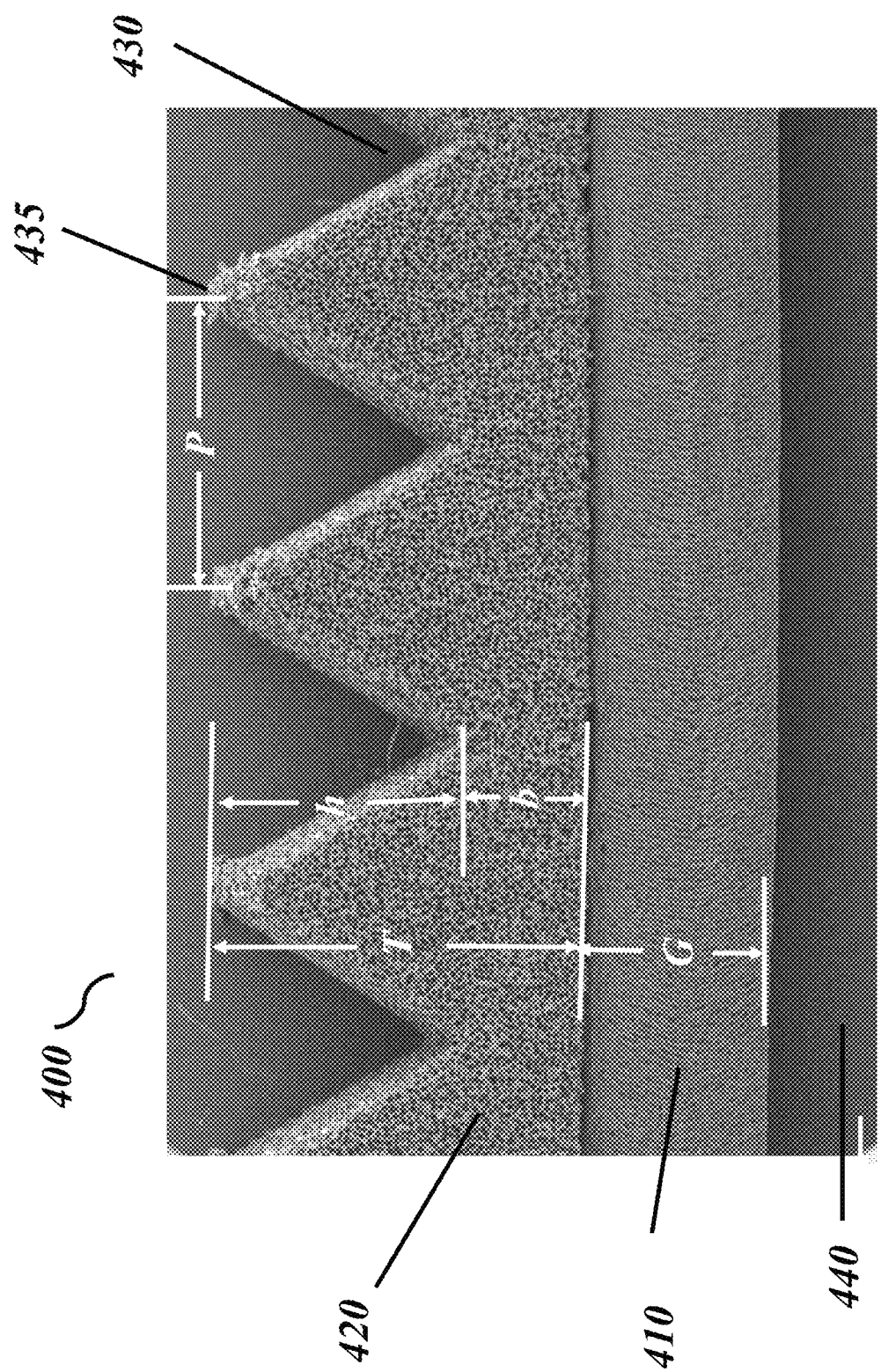
FIG. 5 is a scanning electron microscopy (SEM) image an embodiment of the present invention comprising a two-layer vascular graft with an inner layer of expanded polytetrafluoroethylene (ePTFE) and outer layer of corrugated microporous elastomeric silicone, showing the longitudinal view of the wall cross-section.

FIG. 5 is a scanning electron microscopy (SEM) image of an embodiment according to the present disclosure. As shown, a two-layer vascular graft 400 comprises an inner layer 410 of expanded polytetrafluoroethylene (ePTFE) and an outer layer 420 of corrugated microporous elastomeric silicone, in a longitudinal view of the wall cross-section defining the lumen 440. Each two adjacent ridges 435 of the corrugated contour are separated by a groove 430. To increase kink resistance for this embodiment, it is preferable, but not required, for the height h of the ridges (i.e., the vertical distance from the base of the ridge to the highest point of the ridge) of corrugated contour to be greater than the base thickness b of the corrugated layer. It is also preferable, but not required, for the base thickness b to be less than the core graft thickness G of the inner ePTFE layer. The pitch P or repetition distance between two adjacent ridges of the corrugated contour is preferably similar to the height h of the ridges, in order to balance kink resistance with durability.

The height h of the ridges is preferably within the range of 0.1 to 2 mm, more preferably between 0.3 to 1 mm. The pitch P of the corrugated contour (i.e., the distance between tips of two adjacent ridges or between the respective lowest points of adjacent grooves) is preferably similar to the height of the ridges.

Figure 6:
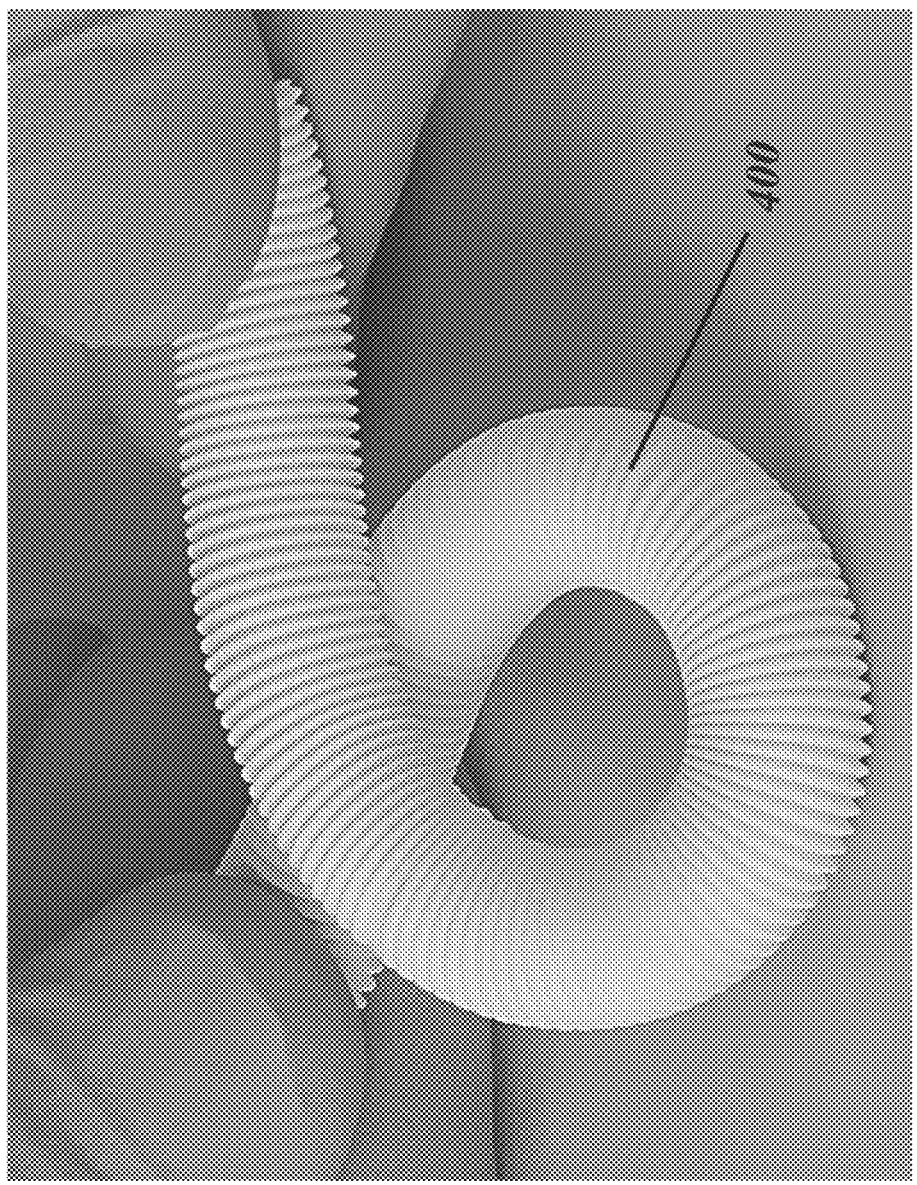
FIG. 6 shows a tight bending radius achieved without kinking for an embodiment of the present invention comprising a two-layer vascular graft with inner layer of expanded polytetrafluoroethylene (ePTFE) and outer layer of corrugated microporous elastomeric silicone.

FIG. 6 shows a tight bending radius without kinking according to an embodiment of the present disclosure. As shown, a two-layer vascular graft 400 comprises an inner layer of expanded polytetrafluoroethylene (ePTFE) and an outer layer of corrugated microporous elastomeric silicone. Due to the corrugated contour of the microporous outer layer, the pitch between ridges shrinks on the inside of the bend and enlarges on the outside of the bend, alleviating stresses that would have otherwise caused kinking in a vascular graft without the corrugated contour.

Figure 7:
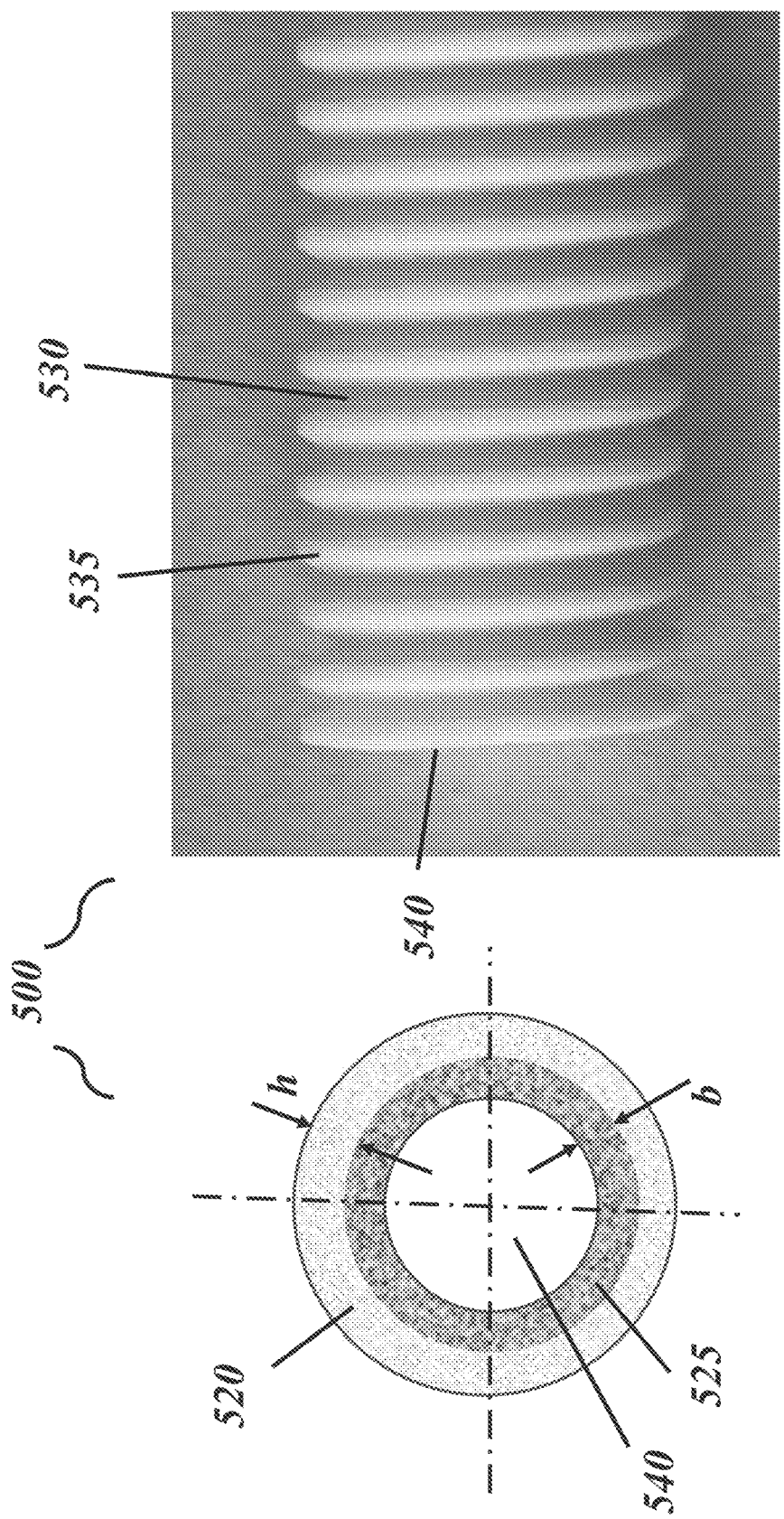
FIG. 7 shows orthogonal views for the embodiment of the present invention comprising a single layer vascular graft comprised of corrugated microporous elastomeric silicone.

FIGS. 7A and 7B show orthogonal views of an embodiment of the present disclosure, shown as a single layer vascular graft 500 comprising corrugated microporous elastomeric silicone. In particular, FIG. 7A shows an end view schematic drawing including a base portion 525 of the layer with base thickness b, and a corrugated part 520 of the layer with ridge height "h," the single layer defining lumen 540. FIG. 7B shows side view photo, indicating ridges 535 separated by grooves 530. For this embodiment, it is preferable that the base thickness b is greater than the ridge height h, to ensure durability.

Figure 8A:
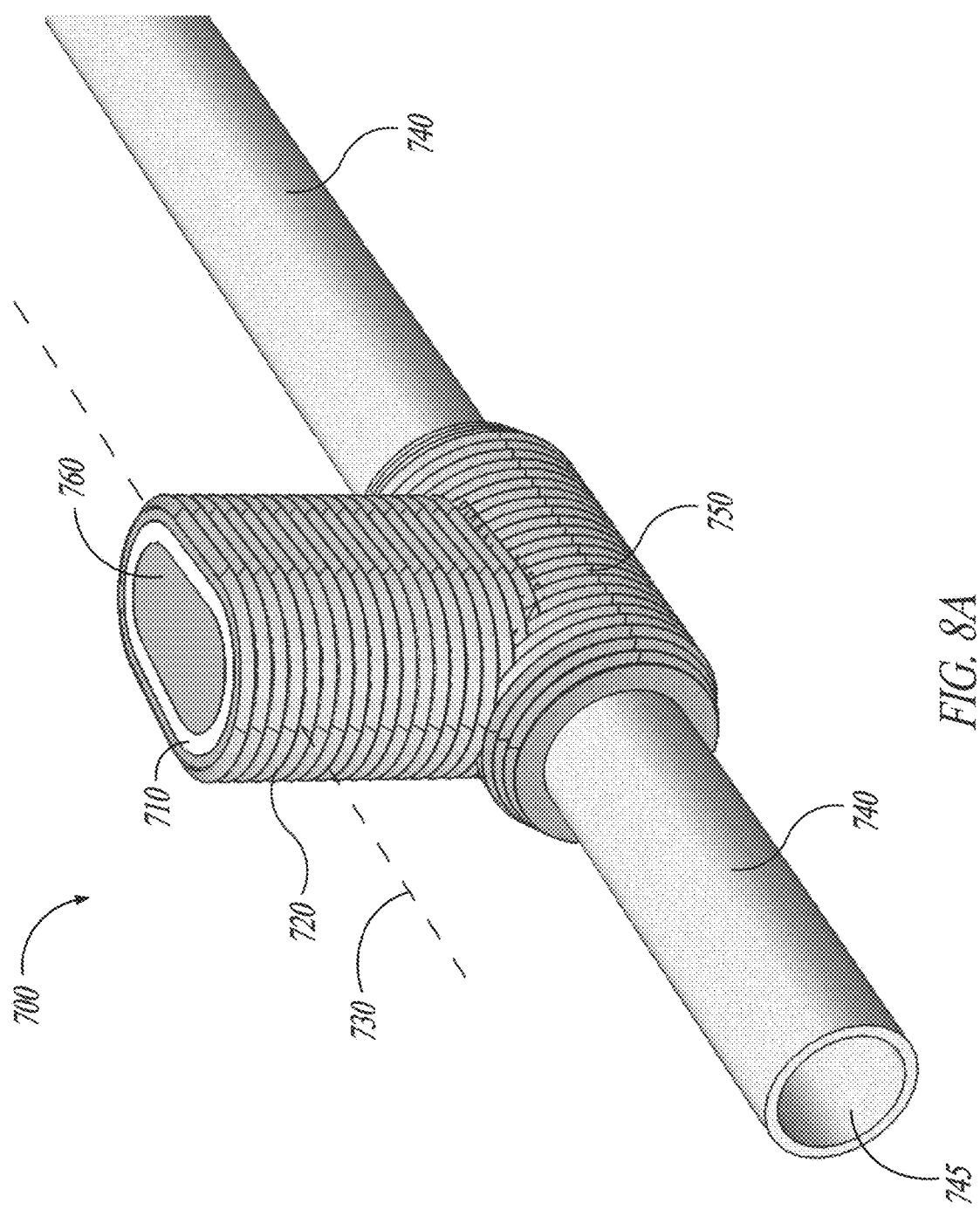

FIG. 8A shows an isometric view schematic drawing according to one embodiment of the present disclosure. As shown, an implantable percutaneous port (700) for providing hemodialysis access comprises a skin-breaching component (710), and a corrugated microporous sheath 720 surrounding the skin-breaching component. The percutaneous port (700) is configured to connect to an arteriovenous vascular graft (740), whereby the skin-breaching component (710) intersects the arteriovenous vascular graft 740 to provide fluid communication. As used herein, the skin-breaching component is configured to extend through the skin and remains in said configuration during dialysis as well as between dialysis. The corrugated microporous sheath (720) comprises a plurality of ridges, each two adjacent ridges being spaced by a groove. In specific embodiments, the ridges are regularly spaced, namely, the pitch between any two adjacent ridges are substantially the same. In a further embodiment, the directions of the ridges (from base to tip) are configured to align with or be substantially parallel to the skin line when the skin-breaching component is inserted into the skin. Consequently, the grooves (also parallel to each other) wrap around the circumference of the skin-breaching component (710).

Like FIG. 8A, FIG. 8B show the port 700 in the "capped" configuration (between dialysis sessions) and in an isometric cutaway view. As shown in FIGS. 8A and 8B, the edge of the skinline 730 interfaces with the corrugated microporous sheath 720. The well of the skin-breaching component 710 of the port is protected with an elastomeric plug 760. A second corrugated microporous sheath 750 covers the rigid port base 715, wherein the port base surrounds the arteriovenous vascular graft 740. Direction of blood flow 748 is indicated by arrow in lumen 745 of the arteriovenous vascular graft 740. Blunt cannula access to the lumen 745 is provided through self-sealing elastomeric valve 770, with the valve retained by the cannula-guide 765.

FIG. 8C shows the port 700 in the "cannulated" configuration (during dialysis), with cannula assembly 800 engaged. When the cannula assembly 800 is engaged, the cannula hub 810 inserts into the well of the port 700, and the dual cannulas 820 penetrate the elastomeric self-sealing valve 770. The arterial cannula 820a provides blood flow from the graft lumen 745 into the arterial blood line 830a, and the venous cannula 820b provides return blood flow to the graft lumen 745 from the venous blood line.

Figure 9:
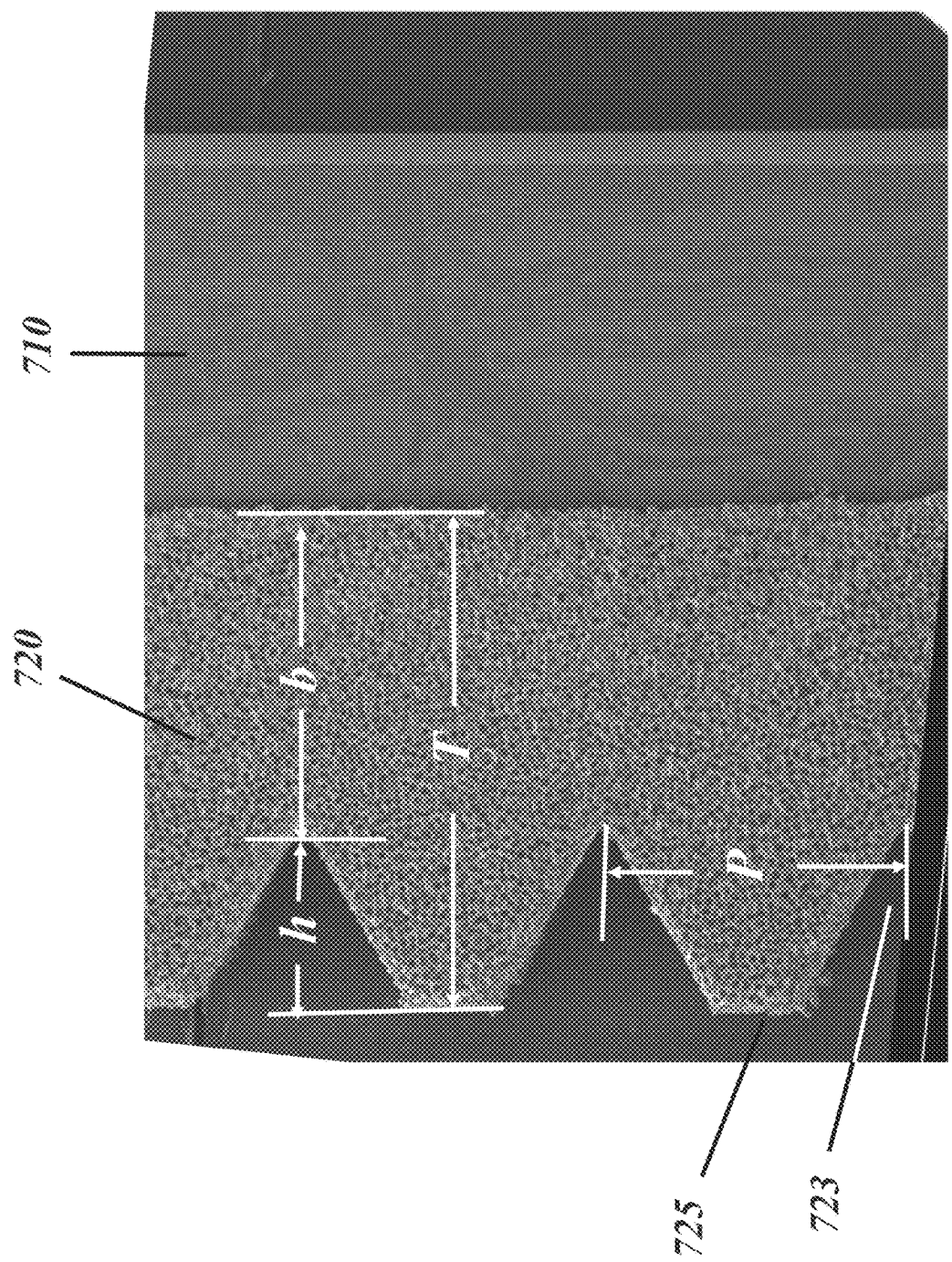
FIG. 9 shows a scanning electron microscopy (SEM) image for the embodiment of the present invention comprising a skin-breaching hemodialysis access port with corrugated microporous silicone elastomer covering the skin-breaching component of the device; a longitudinal wall cross section of the skin-breaching component is shown.

FIG. 9 shows a scanning electron microscopy (SEM) image of a longitudinal wall cross section for the embodiment of the present invention comprising a skin-breaching hemodialysis access port 700 with corrugated microporous silicone elastomer sheath 720 covering the rigid skin-breaching component 710 of the device.

According to this embodiment, the corrugated microporous silicone elastomer sheath 720 comprises a base portion having a thickness (b) and ridges extending from the base portion and having a height (h). The height of the ridges is preferably between 0.5 and 4 mm, more preferably between 1 and 3 mm or between 1 and 2 mm. The base portion typically has a thickness of between 0.8 to 3 times of the height of the ridges. The thickest parts of the sheath have a thickness (T), which is the sum of b and h. The pitch P between neighboring corrugations is preferably similar to the height of the ridges (i.e., between 0.5 and 4 mm).

Figure 10:
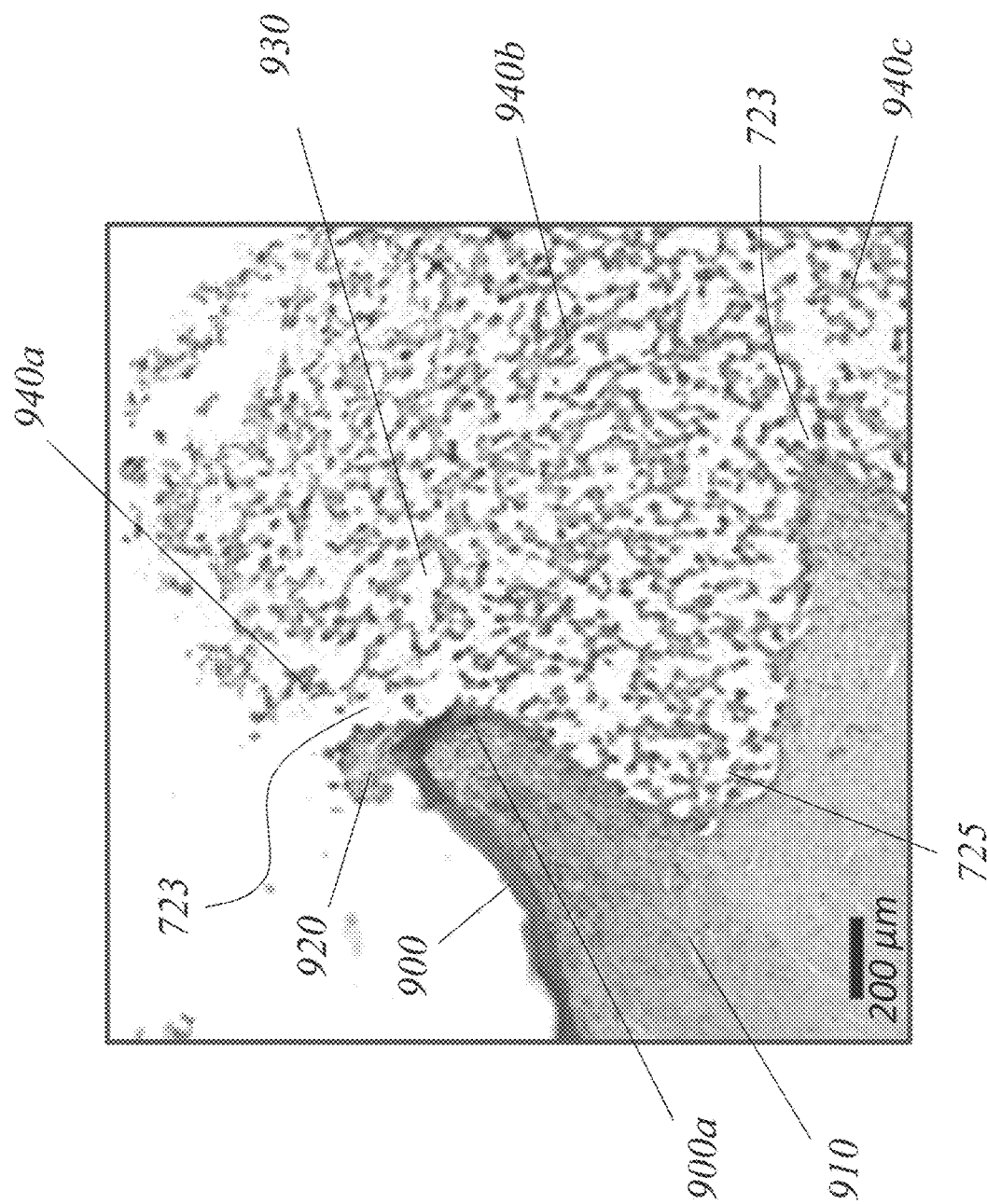
FIG. 10 shows a histological tissue section of the interface between the edge of the skin and the corrugated microporous elastomeric silicone coating of a skin-breaching device.

FIG. 10 shows a histological tissue section of the interface between the edge of the skin and the corrugated microporous elastomeric silicone sheath of a skin-breaching device. The edge of the epidermis 900 nests inside base of a groove 723 between the ridges 725 of the corrugations. The tip 900a of the epidermis 900 shows minimal down-growth due to the advantageous geometry, wherein the ridge 725 underlies and supports the edge of the dermis 910. The microporous biomaterial 930 is infiltrated with vascularized ingrowth 940 (i.e., capillaries inside the micropores). The vascularized ingrowth advantageously extends up beyond the skin interface (above the epidermis 900 on FIG. 10). The extension of vascularized living ingrowth beyond the skinline helps to minimize scab tissue 920, confining it to a small volume. Scab tissue comprises dead host cells and provides an environment for bacteria to reside. Importantly, this embodiment of the disclosure restricts scab tissue to the region outside the skinline.

Figure 11C:
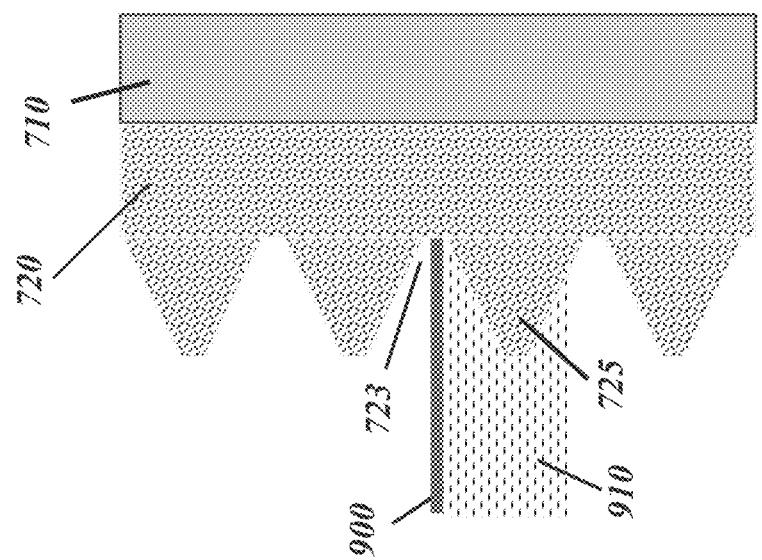
FIGS. 11A-11C show microporous skin edge interfaces for skin-breaching devices with microporosity and macro-topographic features.
Figure 11B:
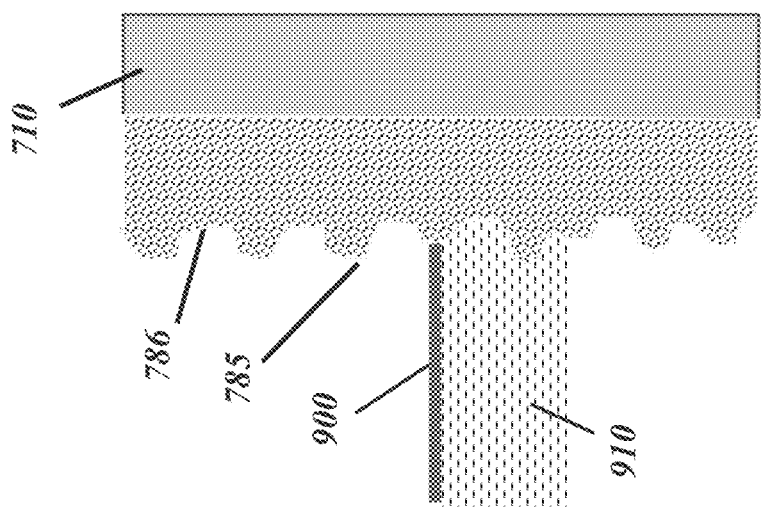
Figure 11A:
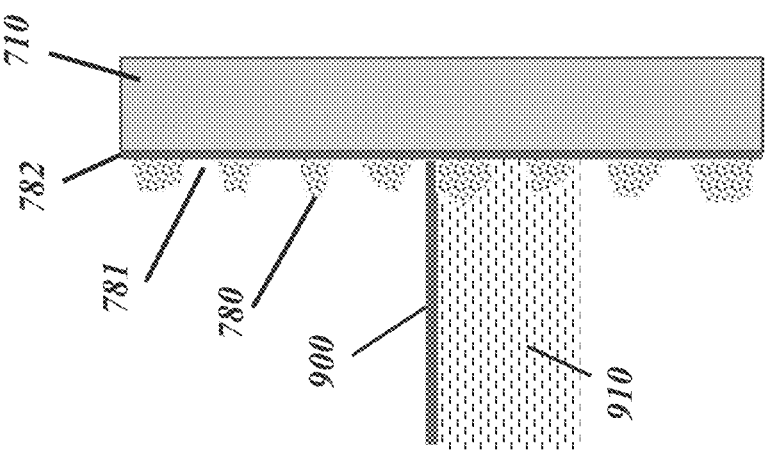

FIGS. 11A-11C illustrate the advantages of an embodiment of the present disclosure over prior art designs having similar yet distinct microporous material at the skin edge interfaces. FIG. 11A schematically shows the junction between the epidermis 900 and a prior art design for an infection-resistant exit site interface comprising a monolayer of granular microporous "peaks" 780 adhered by layer 782 and forming nonporous "valley" floors 781. The lack of connectedness between the microporous granules means that the exteriorized parts of the biomaterial outside the skinline cannot sustain viable tissue. As a result, these can potentially become occupied with dead scab tissue, which can be difficult to keep disinfected.

FIG. 11B schematically shows the junction between a prior art continuously microporous "peaks-and-valleys" material where each peak 785 is surrounded on all sides (separated from neighboring peaks) by a valley 786. In accordance with this design, the edge of the epidermis interfaces alternatingly with both the tops of the peaks and the bases of the valleys. FIG. 11B shows the edge of the epidermis meeting the top of one of these peaks, but it is understood that the edge of the epidermis also interfaces with the base of the valleys at certain points outside the plane of the drawing. This design can result in the interface being subjected to excessive localized stresses at various points along the edge of the epidermis.

FIG. 11C schematically shows a cross section of the continuously porous corrugated exit site interface 720 in accordance with an embodiment of the present disclosure, wherein the groove is continuous and wraps around the entire circumference of the skin-breaching component of the device. It is understood that substantially the entire circumference of the edge of the epidermis nests in the groove between ridges of the corrugated contour.

Grooving or corrugation of exterior contour for the various embodiments of the present invention may be designed in various configurations including but not limited to one or more of the following, which may also be used in combination: spiral corrugation (similar to screw threading), crossed spirals, non-spiral corrugation such as parallel rings or grooves cut circumferentially at longitudinal intervals, cross-hatching consisting of circumferential and longitudinal grooves, or other regularly-spaced pattern of ridges and grooves providing one or more of the advantages mentioned herein.

In particular, for some embodiments, especially where the corrugated microporous elastomer is used as the outer layer or the single layer of a vascular graft, it can be advantageous to combine the circumferentially-aligned ridges and grooves corrugation with longitudinally aligned grooves or notches.

Figures 12A, 12B:
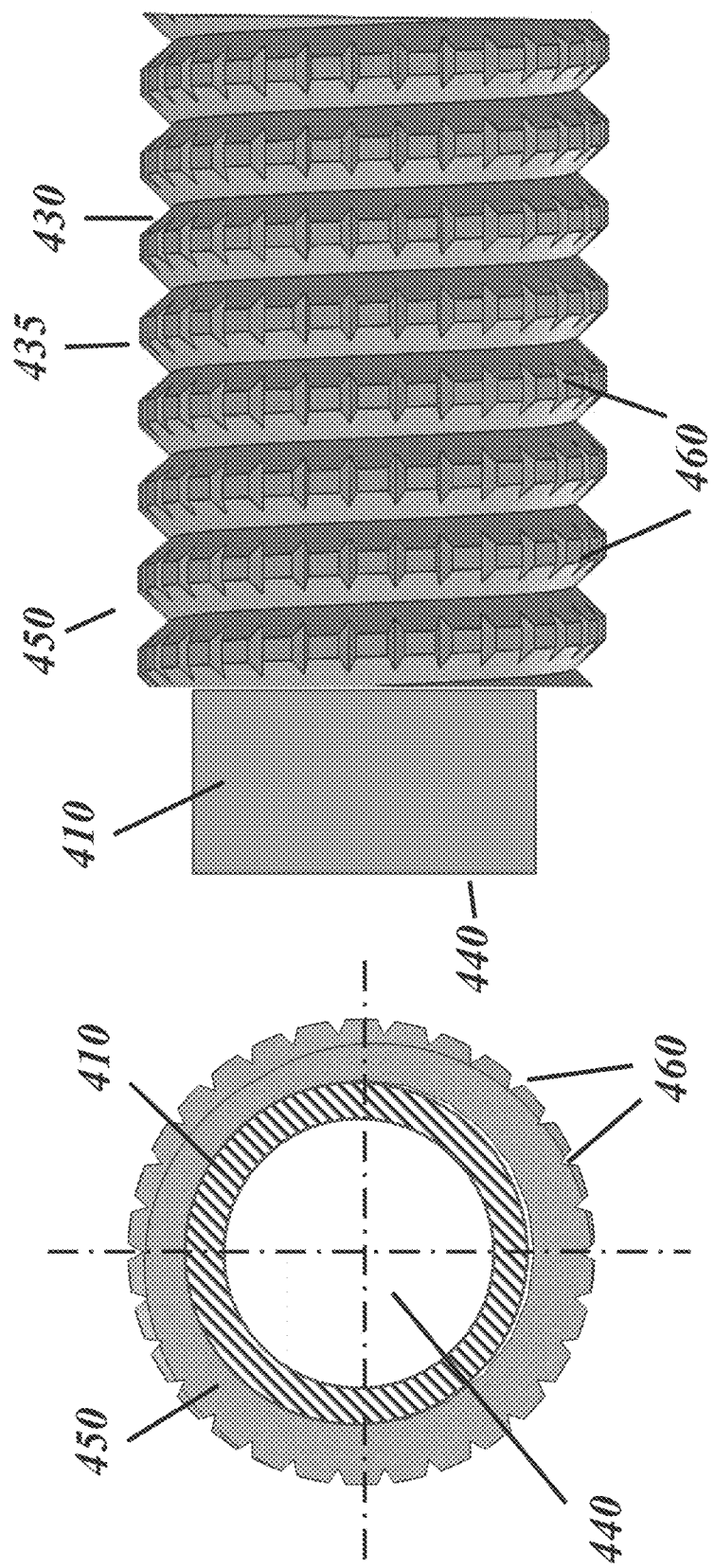
FIGS. 12A-12B show in two different views of an alternative embodiment of a vascular graft porous layer comprising both circumferential and longitudinal grooves.

FIG. 12 A and FIG. 12 B show end and side views respectively of an example similar to that of FIG. 4, but with combined grooves. The outer porous layer 450 is contoured in ridges 435 and grooves 430 as in FIG. 4 and the contour further comprises grooves 460 running longitudinally. It will be understood that similar patterns may also be applied to a device such as shown in FIGS. 8A-8C.

For these embodiments, the circumferentially aligned grooves provide kink resistance while the longitudinally aligned grooves help to provide extra slack in the collagen lattice that is deposited around the exterior of the graft during the early stages of the FBR, resulting in further reduction of constriction forces from capsular contracture upon contraction of the collagen lattice. The height of the circumferentially oriented ridges may differ from the height of the longitudinally oriented ridges.

While the various Figures illustrate particular groove profiles other forms including sinusoidal, trapezoidal, sawtooth, square and other generally periodic shapes may be applied within the scope of this invention. As used herein, "periodic shapes" refers to any repeating pattern of a geometric shape. For instance, ridges regularly separated by grooves could be in configurations of substantially the same size ridges of sinusoidal, trapezoidal, sawtooth, or square shapes being spaced apart at a regular interval. Typically for a skin breaching component, the periodicity occurs along the insertion direction of the device thereby ensuring that the "nesting" effect takes place at the grooves.

The grooving or corrugation can be formed in various ways including molding, laser cutting, waterjet, 3D printing, or machining. In one embodiment, the microporous biomaterial has most of its interstices filled with a material that stiffens the structure sufficiently to allow machining, after which the filler material is removed to restore flexibility. In a preferred embodiment, the beads or porogens that were used to form the pores in the material are not removed until after machining of the grooves or corrugation. In an alternate embodiment, the beads are removed but most of the pores are impregnated with wax prior to groove-cutting, after which the wax is removed.

In certain embodiments, additives, drugs, or fillers may be incorporated into the corrugated microporous layer, such as antibiotics, antiseptic agents, anticoagulants, antiplatelet agents, anti-inflammatory drugs, proangiogenic agents, clotting agents, polymer protectants, hydrophilic coatings, hydrophobic coatings, radio-opaque elements, dyes, fluorescent chemicals, sensing molecules, metabolite-responsive molecules, plasticizers, stiffeners, or other therapeutic agents.

From the foregoing, it will be appreciated that, although specific embodiments of the disclosed technology have been described herein for purposes of illustration, various modifications may be made without deviating from the spirit and scope of the disclosed technology.

The invention claimed is:

1. A tubular implantable device comprising a multi-layer composite wall defining a longitudinal passageway, wherein the multi-layer composite wall includes an inner layer and a microporous sheath layer having a corrugated outer surface, and wherein the microporous sheath layer is formed of a biocompatible elastomeric biomaterial having an open-pore network of interconnected pores extending from the corrugated outer surface to an interface between the inner layer and the microporous sheath layer, wherein the microporous sheath layer includes a base portion and a plurality of ridges extending from the base portion, each two adjacent ridges defining a groove, and wherein the ridges and grooves alternate to provide the corrugated outer surface, and wherein the grooves and ridges are oriented circumferentially or spirally around the tubular implantable device; and wherein the base portion has a thickness that is 0.8-3 times of a mean height of the ridges.

2. The tubular implantable device of claim 1, wherein the biocompatible elastomeric biomaterial comprises a plurality of interconnecting pores, and wherein substantially all the interconnected pores are each connected to at least two other pores, the pores having a mean diameter between about 5 and about 90 micrometers, and any two adjacent pores being connected by a throat having a mean throat diameter of at least 5 micrometers.

3. The tubular implantable device of claim 1 wherein the base portion has a thickness between 0.1-2 millimeters, and the ridges have a mean height of between 0.1 and 2 millimeters.

4. The tubular implantable device of claim 1, wherein the inner layer is made of polyester or expanded polytetrafluoroethylene (ePTFE), and the tubular implantable device is a vascular graft.

5. The tubular implantable device of claim 1, wherein the inner layer forms a dialysis access port adapted to house one or more cannulas, and wherein the dialysis access port is configured to interface with skin.

6. The tubular implantable device of claim 5 wherein the dialysis access port is further connected to a vascular graft, the vascular graft comprising a microporous sheath layer.

7. A vascular graft comprising a single microporous layer defining an inner luminal surface and having a corrugated outer surface, wherein the single microporous layer is formed of a biocompatible elastomeric biomaterial having an open-pore network of a plurality of interconnected pores extending from the inner luminal surface to the corrugated outer surface; wherein substantially all the plurality of the interconnected pores are each connected to at least two other pores, the pores having a mean diameter between about 5 and about 90 micrometers, and wherein any two adjacent pores are connected by a throat, the throat having a mean diameter of at least 5 micrometers, wherein the single microporous layer includes a base portion defining the inner luminal surface and a plurality of ridges extending from the base portion, each two adjacent ridges defining a groove, and wherein the ridges and grooves alternate to provide the corrugated outer surface, and wherein the grooves and ridges are oriented circumferentially or spirally around the vascular graft, and wherein the ridges have a mean height of between 0.1 and 2 millimeters and wherein the base portion has a thickness of between 0.1 and 2 millimeters.

* * * * *